US009439792B2

(12) United States Patent
Pacetti et al.

(10) Patent No.: US 9,439,792 B2
(45) Date of Patent: Sep. 13, 2016

(54) METHOD OF MAKING IMPLANTABLE PROSTHESIS WITH DEPOT RETENTION FEATURE

(71) Applicant: Abbott Cardiovascular Systems Inc., Santa Clara, CA (US)

(72) Inventors: Stephen D. Pacetti, San Jose, CA (US); Cameron K. Kerrigan, Burlingame, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 76 days.

(21) Appl. No.: 14/053,019

(22) Filed: Oct. 14, 2013

(65) Prior Publication Data
US 2014/0033504 A1     Feb. 6, 2014

Related U.S. Application Data

(62) Division of application No. 12/752,757, filed on Apr. 1, 2010, now Pat. No. 8,562,670.

(51) Int. Cl.
*A61F 2/91*     (2013.01)
*A61F 2/915*     (2013.01)

(52) U.S. Cl.
CPC ............. *A61F 2/91* (2013.01); *A61F 2/915* (2013.01); *A61F 2210/0004* (2013.01); *A61F 2210/0076* (2013.01); *A61F 2230/0013* (2013.01); *A61F 2250/0068* (2013.01); *Y10T 29/49826* (2015.01)

(58) Field of Classification Search
CPC .. A61F 2/91; A61F 2/915; A61F 2210/0076; A61F 2230/0013; A61F 2210/0004; A61F 2250/0068; Y10T 29/49826
See application file for complete search history.

(56) References Cited

U.S. PATENT DOCUMENTS

| 7,163,555 | B2 | 1/2007 | Dinh | |
|---|---|---|---|---|
| 7,909,865 | B2 * | 3/2011 | Shanley | 623/1.42 |
| 8,353,949 | B2 * | 1/2013 | Weber et al. | 623/1.15 |
| 8,435,550 | B2 * | 5/2013 | Cheng et al. | 424/423 |
| 2007/0224235 | A1 | 9/2007 | Tenney | |

FOREIGN PATENT DOCUMENTS

WO     WO 2009/094270 A1     7/2009

OTHER PUBLICATIONS

English Translation of Notice of Reasons for Rejection from Japan Patent Office for Japan Patent Application No. P2013-502640, dispatched Oct. 21, 2014, 5 pages.

* cited by examiner

*Primary Examiner* — Richard Chang
(74) *Attorney, Agent, or Firm* — Squire Patton Boggs (US) LLP

(57) ABSTRACT

A prosthesis for intraluminal drug delivery can comprise a plurality of interconnected struts that form a tubular scaffold structure. The struts include through-holes with an inner surface configured to retain a bioabsorbable depot. The bioabsorbable depot includes a drug-polymer composition that hydrolytically degrades upon implantation. The inner surface of the through-hole can be an entirely smooth and continuous area that is concave or convex, with no geometric discontinuities. The inner surface of the through-hole can include any number of constricted and distended regions to form grooves of a size and shape carefully selected to engage a corresponding geometric feature of the bioabsorbable depot.

10 Claims, 12 Drawing Sheets

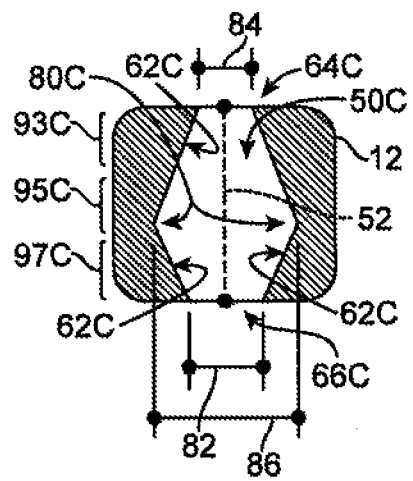
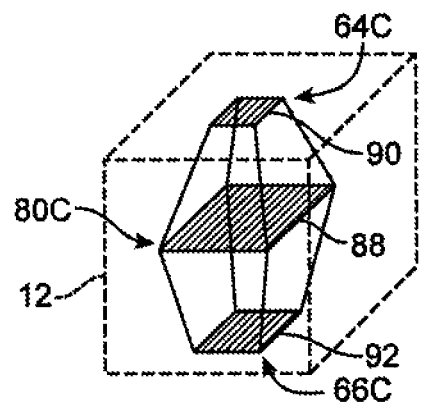
FIG. 13A  FIG. 13B
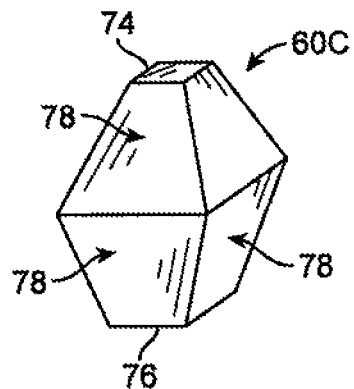
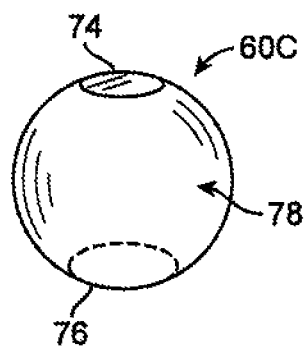
FIG. 14A  FIG. 14B
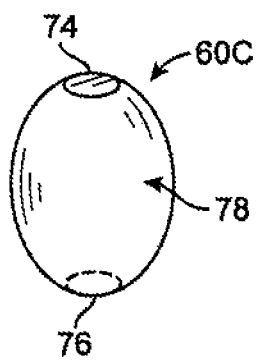
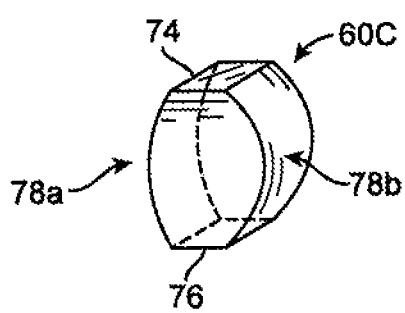
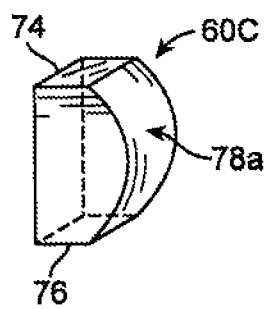
FIG. 14C  FIG. 14D  FIG. 14E

METHOD OF MAKING IMPLANTABLE PROSTHESIS WITH DEPOT RETENTION FEATURE

CROSS-REFERENCE TO RELATED APPLICATIONS

This application is a divisional of application Ser. No. 12/752,757, filed on Apr. 1, 2010, which application is incorporated herein by reference.

FIELD OF THE INVENTION

Briefly and in general terms, the present invention generally relates to an implantable prosthesis and, more particularly, to a drug eluting stent.

BACKGROUND OF THE INVENTION

In percutaneous transluminal coronary angioplasty (PTCA), a balloon catheter is inserted through a brachial or femoral artery, positioned across a coronary artery occlusion, and inflated to compress against atherosclerotic plaque to open, by remodeling, the lumen of the coronary artery. The balloon is then deflated and withdrawn. Problems with PTCA include formation of intimal flaps or torn arterial linings, both of which can create another occlusion in the lumen of the coronary artery. Moreover, thrombosis and restenosis may occur several months after the procedure and create a need for additional angioplasty or a surgical bypass operation. Stents are used to address these issues. Stents are small, intricate, implantable medical devices and are generally left implanted within the patient to reduce occlusions, inhibit thrombosis and restenosis, and maintain patency within vascular lumens such as, for example, the lumen of a coronary artery.

The treatment of a diseased site or lesion with a stent involves both delivery and deployment of the stent. Stent delivery refers to introducing and transporting the stent through an anatomical lumen to a desired treatment site, such as a lesion in a vessel. An anatomical lumen can be any cavity, duct, or a tubular organ such as a blood vessel, urinary tract, and bile duct. Stent deployment corresponds to expansion of the stent within the anatomical lumen at the region requiring treatment. Delivery and deployment of a stent are accomplished by positioning the stent about one end of a catheter, inserting the end of the catheter through the skin into an anatomical lumen, advancing the catheter in the anatomical lumen to a desired treatment location, expanding the stent at the treatment location, and removing the catheter from the lumen with the stent remaining at the treatment location. These stents may be constructed of a fine mesh network of struts, which provide support or push against the walls of the anatomical lumen in which the stent is implanted.

In the case of a balloon expandable stent, the stent is mounted about a balloon disposed on the catheter. Mounting the stent typically involves compressing or crimping the stent onto the balloon prior to insertion in an anatomical lumen. At the treatment site within the lumen, the stent is expanded by inflating the balloon. The balloon may then be deflated and the catheter withdrawn from the stent and the lumen, leaving the stent at the treatment site. In the case of a self-expanding stent, the stent may be secured to the catheter via a retractable sheath. When the stent is at the treatment site, the sheath may be withdrawn which allows the stent to self-expand.

Stents are often modified to provide drug delivery capabilities to further address thrombosis and restenosis. Stents may be coated with a polymeric carrier impregnated with a drug or therapeutic substance. A conventional method of coating includes applying a composition including a solvent, a polymer dissolved in the solvent, and a therapeutic substance dispersed in the blend to the stent by immersing the stent in the composition or by spraying the composition onto the stent. The solvent is allowed to evaporate, leaving on the stent strut surfaces a coating of the polymer and the therapeutic substance impregnated in the polymer.

The application of a uniform coating with good adhesion to a substrate can be difficult for small and intricate medical devices, such as certain stents for coronary and peripheral arteries. Such stents can be quite small. Stents for the coronary vessel anatomy typically have an overall diameter of only a few millimeters and a total length of several millimeters to tens of millimeters. Stents for the peripheral vessel anatomy are generally greater in diameter and length. Such peripheral stents may have a diameter up to 10 mm and a length of up to a few hundred millimeters.

Some drug eluting stents include pockets or depressions which are filled with a drug-containing composition, referred to as a depot or microdepot. Depending on their size, the drug-containing compositions may cause an embolic hazard if they dislodge as particles from the stent and flow into a patient's blood stream. This can be of particular concern for drug-containing compositions composed of bioabsorbable polymers with mechanical properties that are altered by the bioabsorption process after implantation. Accordingly, there is a need for stent designs that retain the microdepots.

SUMMARY OF THE INVENTION

Briefly and in general terms, the present invention is directed to an implantable, intraluminal prosthesis and a method of making a prosthesis.

In aspects of the present invention, an implantable, intraluminal prosthesis comprises a plurality of interconnected struts and a plurality of bioabsorbable depots. The plurality of interconnected struts form a tubular structure, each of the struts having a luminal surface facing radially inward and an abluminal surface facing radially outward. At least some of the struts have through-holes with opposite end openings located at the abluminal and luminal surfaces. Each of the through-holes has an inner surface with a geometric retention feature at a middle segment of the through-hole. The geometric feature has a predetermined shape corresponding to a distention of the through-hole or corresponding to a constriction of the through-hole. Each bioabsorbable depot is carried in a separate one of the through-holes, wherein the geometric retention feature of each of the through-holes is configured to retain the bioabsorbable depot in the through-hole after a decrease in molecular weight, strength or mass of the bioabsorbable depot.

In aspects of the present invention, an implantable, intraluminal prosthesis comprises a tubular frame of interconnected structural members. The tubular frame is configured to expand radially. At least some of the structural members have a through-hole formed therein, each through-hole comprising two end openings and an inner surface extending between the end openings, the inner surface having an indentation of a preselected size and shape. The prosthesis further comprises a plurality of bioabsorbable depots, each bioabsorbable depot retained in a separate one of the through-holes. Each bioabsorbable depot comprises a therapeutic agent and a bioabsorbable polymer. Each bioabsorbable depot comprises a protrusion that extends into the indentation of the through-hole in which the bioabsorbable depot is retained. The protrusion and the indentation engaged with each other to prevent the bioabsorbable depot from sliding out of at least one of the end openings.

In aspects of the present invention, a method of making an implantable, intraluminal prosthesis comprises forming a tubular frame of interconnected structural members, forming through-holes in the structural members, and forming an indentation in an inner surface of each of the through-holes. The method further comprises forming a bioabsorbable depot in each of the through-holes, which comprises forming a protrusion of the bioabsorbable depot that engages the indentation of the through-hole in which the bioabsorbable depot is retained. Engagement of the protrusion with the indentation prevents the bioabsorbable depot from sliding out of the through-hole.

The features and advantages of the invention will be more readily understood from the following detailed description which should be read in conjunction with the accompanying drawings.

BRIEF DESCRIPTION OF THE DRAWINGS

FIGS. 13A and 13B are cross-sectional and perspective views, respectively, of a prosthesis structural member, showing a through-hole with a depot retention feature in the form of a distension in a middle segment of the through-hole, the distension created by an indentation in an inner surface of the through-hole.

FIGS. 14A-14E are perspective views of various bioabsorbable depots that can be retained in a through-hole having a distension in a middle segment of the through-hole.

DETAILED DESCRIPTION OF THE PREFERRED EMBODIMENTS

Figure 1:
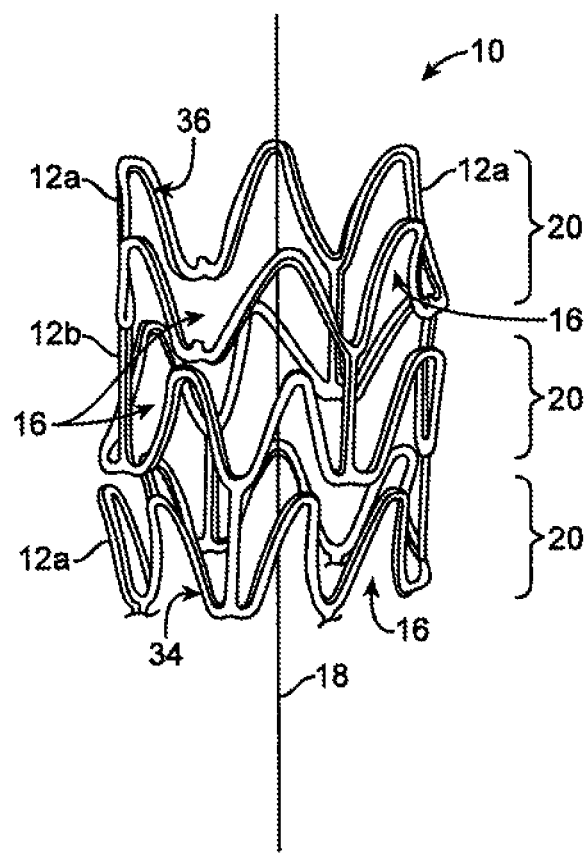
FIG. 1 is a is a perspective view of an end portion of a stent.

Referring now in more detail to the exemplary drawings for purposes of illustrating embodiments of the invention, wherein like reference numerals designate corresponding or like elements among the several views, there is shown in FIG. 1 an upper portion of a stent 10 having an overall body shape that is hollow and tubular. The stent can be balloon expandable or self-expandable.

The present invention encompasses stents having any particular geometrical configuration, such as a zig-zag, sinusoidal or serpentine strut configuration, and should not be limited to the patterns illustrated herein. The variation in stent patterns is virtually unlimited.

Figure 2:
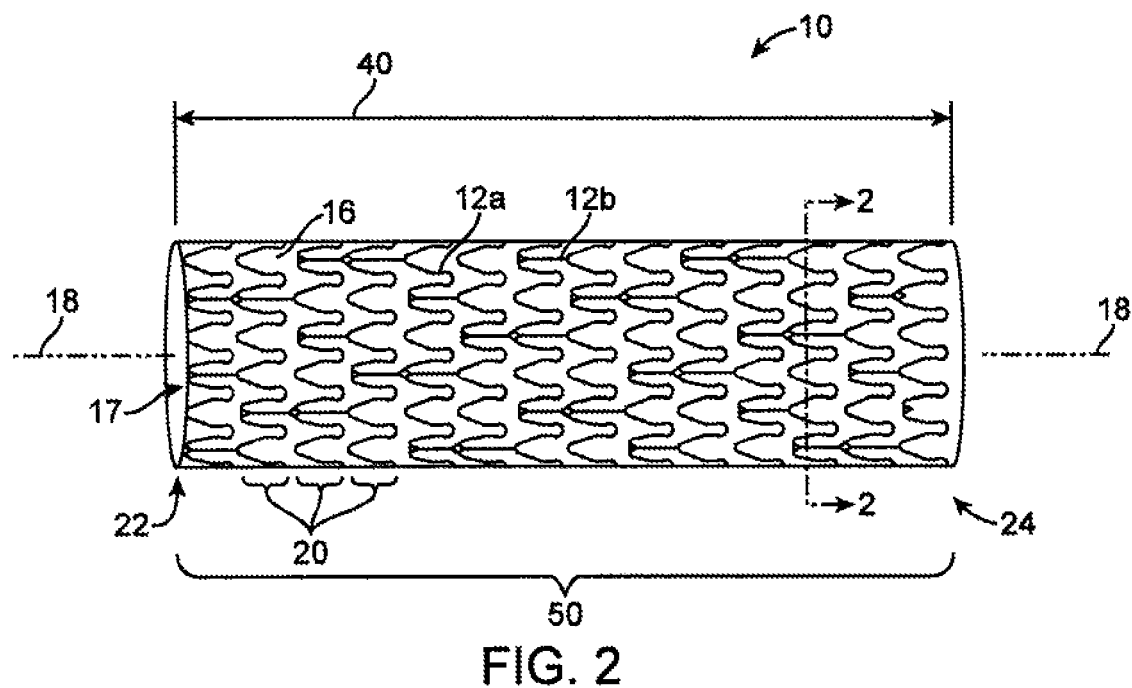
FIGS. 2 and 3 are perspective and radial cross-sectional views, respectively, of a stent.

FIGS. 1 and 2 show stents with two different stent patterns. The stents are illustrated in an uncrimped or expanded state. In both FIGS. 1 and 2 the stent 10 includes many interconnecting struts 12a, 12b separated from each other by gaps 16. The struts 12a, 12b form a tubular frame and can be made of any suitable material, such as a biocompatible metal or biocompatible polymer. The material can be non-bioabsorable or bioabsorbable.

As used herein, the terms "bioabsorbable" and "biodegradable" are used interchangeably and refer to materials that are capable of being degraded or absorbed when exposed to bodily fluids such as blood, and components thereof such as enzymes, and that can be gradually resorbed, absorbed, and/or eliminated by the human or animal body.

The stent 10 has an overall longitudinal length 40 measured from opposite ends, referred to as the distal and proximal ends 22, 24. The stent 10 has an overall body 50 having a tube shape with a central passageway 17 passing through the entire longitudinal length of the stent. The central passageway has two circular openings, there being one circular opening at each of the distal and proximal ends 22, 24 of the overall tubular body 50. A central axis 18 runs through the central passageway in the center of the tubular frame or body 50. At least some of the struts 12a are arranged circumferentially in series to form sinusoidal or serpentine ring structures 20 that encircle the central axis 18. The ring structures 20 are connected to each other by other struts 12b, referred to as links, that are substantially straight and are oriented longitudinally. In some embodiments, the ring structures 20 are configured to be crimped and subsequently radially expanded. In some embodiments, the ring structures 20 are connected directly to one another without intervening links 12b.

Figure 3:
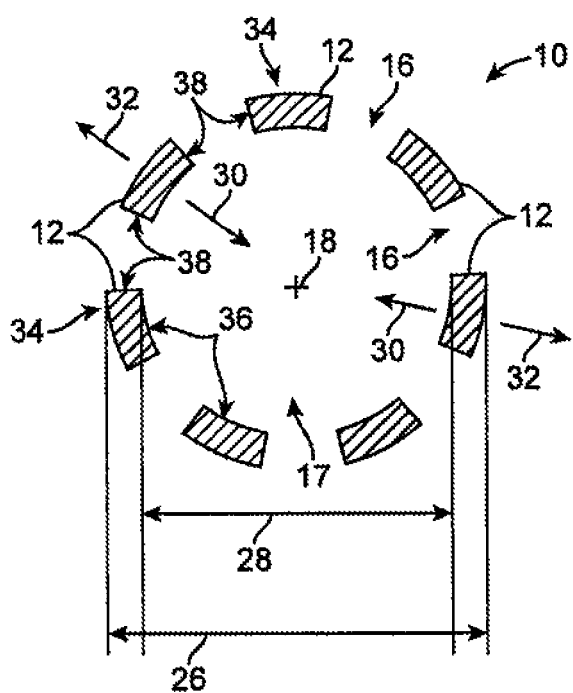

FIG. 3 is an exemplary radial cross-sectional view of the stent 10 along line 2-2 in FIG. 2. There can be any number of struts 12 along line 2-2, which runs perpendicular to the central axis 18 of the stent 10. In FIG. 3, the cross-section of seven struts 12 are shown for ease of illustration. The struts 12 in cross-section are arranged in a circular pattern having an outer diameter 26 and an inner diameter 28. The circular pattern encircles the central axis 18. A portion of the surface of each strut faces radially inward in a direction 30 facing toward the central axis 18. A portion of the surface of each strut faces radially outward in a direction 32 facing away from the central axis 18. The various strut surfaces that face radially outward are individually referred to as abluminal surfaces 34. The abluminal surfaces of the struts collectively form the abluminal surface of the stent tubular body 50. The various strut surfaces that face radially inward are individually referred to as luminal surfaces 36. The luminal surfaces of the struts collectively form the luminal surface of the stent tubular body 50. Side surfaces 38 connect the luminal surfaces 36 to the abluminal surfaces 34. In FIG. 3, the side surfaces 38 are flat and extend radially.

The terms "axial" and "longitudinal" are used interchangeably and relate to a direction, line or orientation that is parallel or substantially parallel to the central axis of a stent or a central axis of a cylindrical or tubular structure. The term "circumferential" relates to the direction along a circumference of a stent or a circular structure. The terms "radial" and "radially" relate to a direction, line or orientation that is perpendicular or substantially perpendicular to the central axis of a stent or a central axis of a cylindrical or tubular structure.

Figure 4:
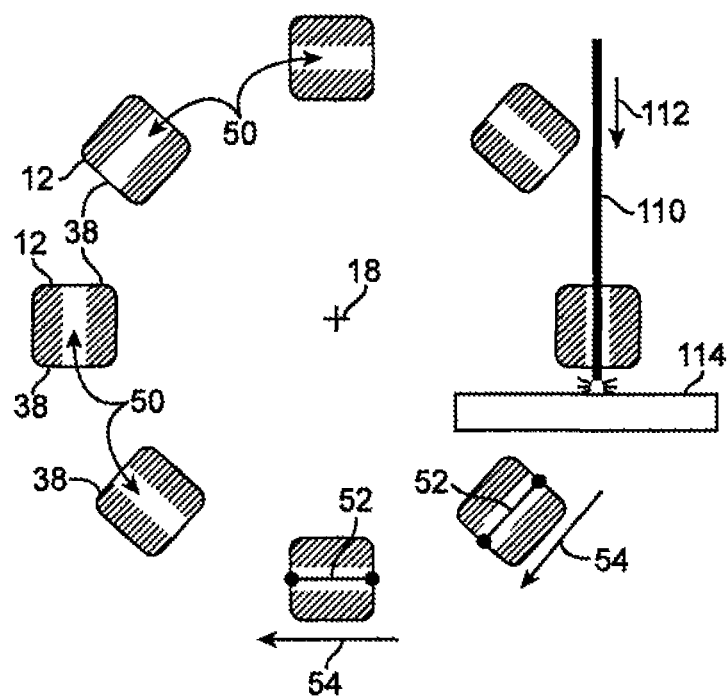
FIG. 4 is a radial cross-sectional view of a stent, showing stent struts with transverse through-holes for carrying a therapeutic agent to be delivered intraluminally.
Figure 5:
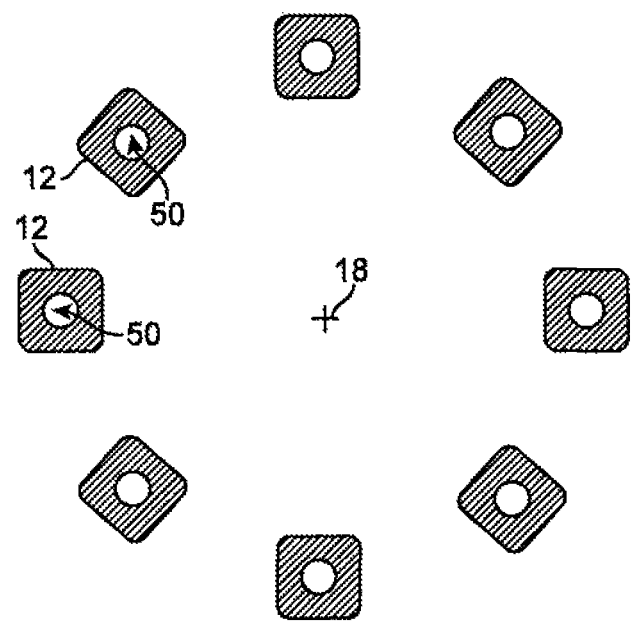
FIG. 5 is a radial cross-sectional view of a stent, showing stent struts with axial through-holes for carrying a therapeutic agent.
Figure 6:
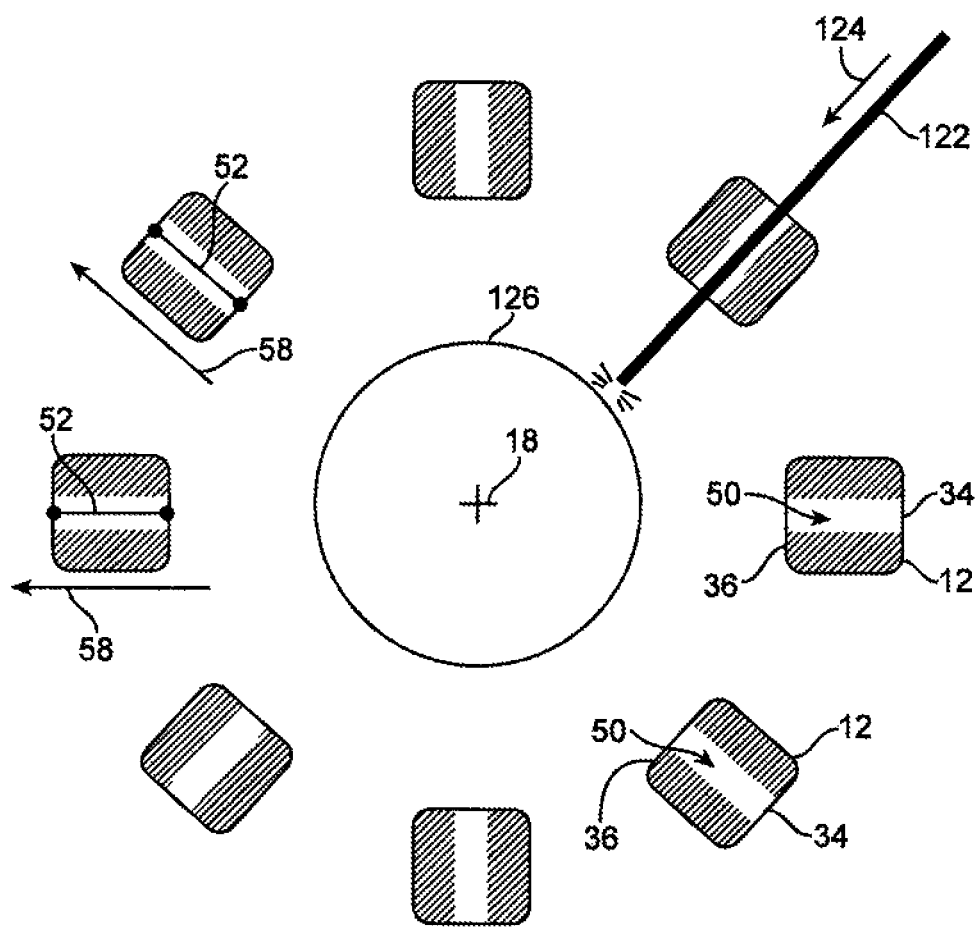
FIG. 6 is a radial cross-sectional view of a stent, showing stent struts with radial through-holes for carrying a therapeutic agent.

As shown for example in FIGS. 4-6, at least some of the struts can have through-holes 50. The through-holes 50 are different from the gaps 16 (FIGS. 2 and 3) in that the through-holes 50 are formed into individual struts 12 whereas the gaps 16 are disposed between two of more of the struts 12. Also, the gaps 16 change greatly in size during crimping and radial expansion of the stent body whereas the through-holes 50 do not change in size as a result of crimping and radial expansion of the stent body. Further, the through-holes 50 have a cross-dimension or diameter that is no greater than the cross-dimension or width of an individual strut, whereas the gaps 16 have a cross-dimension that often exceeds that of the struts.

The term "through-hole" refers to a passageway that extends entirely through a structure and has openings at opposite ends of the passageway. Through-holes can be straight with no bend, as shown in FIGS. 4-6, or they can be slightly curved or bent. Through-holes are different from blind-holes which have only a single opening and do not extend entirely through a structure. Each of the through-holes shown in FIGS. 4-7, 11A, 13A, 15A and 18A have exactly two openings and do not connect to or intersect with any other through-hole. In some embodiments, a through-hole intersects with or extends into another through-hole.

In some embodiments, the openings at opposite ends of the through-holes 50 have a diameter from 10 microns to 300 microns, and more narrowly from 40 microns to 200 microns. In some embodiments, the through-holes have an average diameter across the entire length of the through-holes from 10 microns to 300 microns, and more narrowly from 40 microns to 200 microns.

In some embodiments, as shown in FIG. 4, through-holes 50 are oriented transversely or extend transversely through the struts 12. Each of the transverse through-holes 50 has an end-to-end inline length 52 that extends in a transverse direction 54. The phrase "transverse direction" refers to a direction that runs substantially at a tangent to a circle around the central axis 18 and which does not intersect the central axis 18. The term "end-to-end inline length" refers to a straight line segment that starts from the center of one through-hole opening, ends at the center of the opposite through-hole opening, and runs through the through-hole passageway without intersecting walls of the through-hole. As shown in FIG. 4, the transverse through-holes pass through side surfaces 38 that face in opposite directions. In other embodiments, all or only some of the through-holes in an implantable prosthesis are oriented transversely.

In some embodiments, as shown in FIG. 5, through-holes 50 are oriented axially or extend axially through the struts 12. Each of the axial through-holes 50 has an end-to-end inline length that extends in an axial direction that is substantially parallel to the central axis 18. The axial through-holes pass through side surfaces 38 that face in opposite axial directions. In other embodiments, all or only some of the through-holes in an implantable prosthesis are oriented axially.

In some embodiments, as shown in FIG. 6, through-holes 50 are oriented radially or extend radially through struts 12. Each of the radial through-holes 50 has an end-to-end inline length 52 that extends in a radial direction 58 away from the central axis 18. The radial through-holes pass through the abluminal surfaces 34 and luminal surfaces 36 of the struts 12. In other embodiments, all or only some of the through-holes in an implantable prosthesis are oriented radially.

In some embodiments, where the implantable prosthesis is tubular, the end openings of the through-holes are located at the abluminal surface or luminal surface exclusively. In some embodiments, where the implantable prosthesis includes interconnecting struts, the end openings of the through-holes are located at the strut side surfaces exclusively. In other embodiments, an implantable prosthesis has a mix of radial through-holes and non-radial through-holes.

Figure 7:
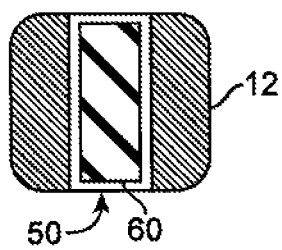
FIG. 7 is a radial cross-sectional view of a prosthesis structural member, showing a single through-hole that may be oriented radially, axially, or transversely, the through-hole having no depot retention feature.

The through-holes described above and below are configured to carry a bioabsorbable composition, referred to as a bioabsorbable depot 60, such as shown in FIG. 7. The composition includes a drug which is released into the anatomical lumen and vessel wall as the composition degrades over time.

In the above and following description, the word "drug" in the singular includes the plural unless expressly stated otherwise. It is to be understood that the word "drug" includes one such drug, two such drugs, or under the right circumstances as determined by those skilled in the treatment of diseased tissues, even more such drugs unless it is expressly stated or is unambiguous from the context that such is not intended.

Figure 8:
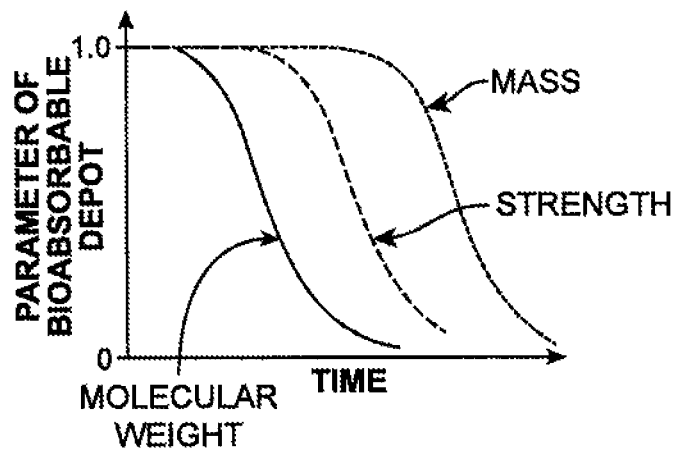
FIG. 8 is a graph showing changes in parameter values over time, the parameter values being molecular weight, strength, and mass of a bioabsorbable polymer.

In some embodiments, the composition includes a bioabsorbable polymer in which the drug is dispersed, mixed, or encased. An example of such a polymer is poly(D,L-lactide-co-glycolide), also referred to as PLGA. After implantation of the prosthesis, the bioabsorbable depot could become loose as shown in FIG. 7. This is because polymers that undergo a hydrolytic degradation mechanism, such as PLGA, lose molecular weight, mechanical strength, and mass over time, such as generally depicted in FIG. 8. It is apparent from FIG. 8 that the strength of the polymer will start to diminish before mass loss takes place. As molecular weight drops, the polymer gets weaker and weaker, essentially becoming softer. Also as the molecular weight drops, there is an increase in water content due to an increase in carboxyl and hydroxyl polymer endgroups. For PLGA, by the time that mass loss occurs at a significant rate, the molecular weight has dropped to as low as 20K Daltons, so that the microdepot is a soft mass. Thus, a bioabsorbable depot may detach or dislodge if it is made of a bioabsorbable polymer.

A way to keep the bioabsorbable depot 60 from dislodging after softening or loosing mass is to have through-holes that have variable cross-sections and geometric discontinuities. The variable cross-section results from having inner walls of the through-holes be a particular configuration (e.g., as shown in FIGS. 9, 11, 13, 15 and 18) that prevents or inhibits a bioabsorbable depot from dislodging as a particle having a size that could present an embolic hazard. The embolic hazard depends on the number and size of released particles. As particle size increases, the volume of tissue that is embolized by occlusion of distal vasculature rises in a non-linear, almost exponential fashion. Debris in the blood stream that is 100 microns or more in size, in particular, can present an embolic hazard. Also, particles as small as 10 microns can be hazardous if released in large numbers.

The various depot retention features described below can be applied to any of the through-holes shown in FIGS. 4-7.

Figure 9A:
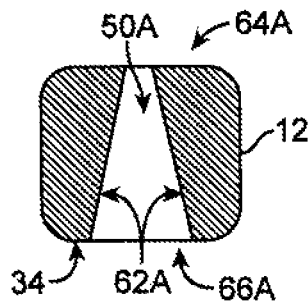
FIGS. 9A-9D are radial cross-sectional views of a prosthesis structural member, showing a through-hole with a depot retention feature in the form of a smooth, continuously tapered inner surface.
Figure 9B:
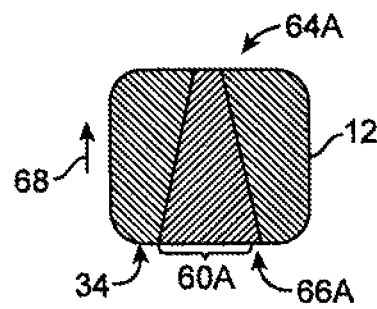
Figure 9C:
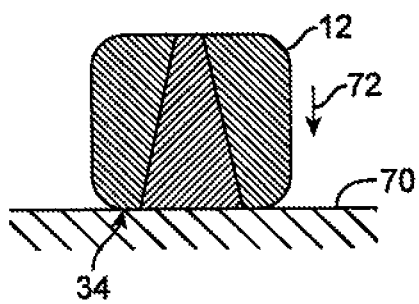
Figure 9D:
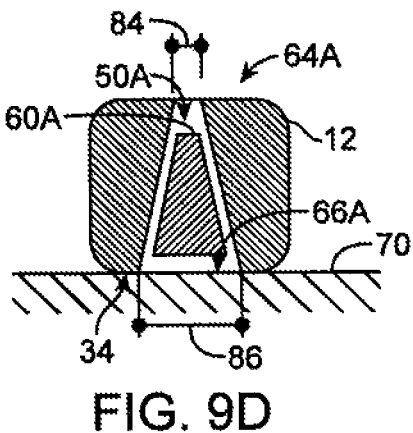

In some embodiments, as shown in FIG. 9A, a through-hole 50A (shown without a bioabsorbable depot) has an inner surface 62A with a tapered cross-sectional configuration. As shown in FIG. 9B, a bioabsorbable depot 60A inside the through-hole 50A takes on a corresponding tapered cross-sectional shape. There are two openings 64A, 66A at opposite ends of the through-hole 50A. One of the openings 66A is larger than the other 64A, so that the bioabsorbable depot is prevented or inhibited from sliding out in the direction of arrow 68. The relatively narrow segment of the through-hole, adjacent the smaller opening 64A, serves as a geometric retention feature that keeps the depot from sliding out in the direction of arrow 68. In use as shown in FIG. 9C, the larger opening 66A is at an abluminal surface 34 of an implantable prosthesis so that the larger opening 66A is up against or immediately adjacent an anatomical structure 70, such as blood vessel wall, so as to keep the bioabsorbable depot 60A from sliding out in the direction of arrow 72. The smaller opening 64A can be sized such that after significant loss or strength and/or mass over time, as shown in FIG. 9D, the bioabsorbable depot 60A cannot pass through the smaller opening 64A and is retained in the tapered through-hole 50A.

In some embodiments, the cross-dimension 84 of the smaller opening 64A is from about 10 microns to 200 microns, more narrowly from about 10 microns to 100 microns, more narrowly from about 10 microns to about 80 microns, and more narrowly from about 10 microns to about 50 microns. The upper size limit for the cross-dimension 84 is optionally below 100 microns since debris of 100 microns or more in size may present a particular embolic hazard. In some embodiments, the cross-dimension 84 of the smaller opening 64A is at least half that of the cross-dimension 86 of the larger opening 66A, giving a size ratio of 1:2. Other suitable size ratios include without limitation 1:3, 1:4, 1:5, and 1:10.

Figure 10A:
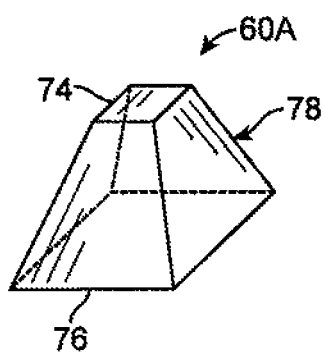
FIGS. 10A-10E are perspective views of various bioabsorbable depots that can be retained in a through-hole having a smooth, continuously tapered inner surface.
Figure 10B:
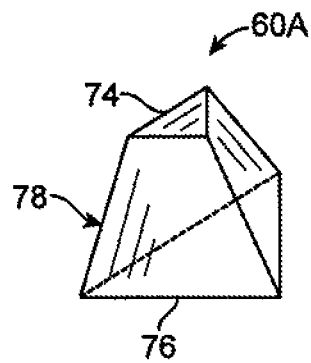
Figure 10C:
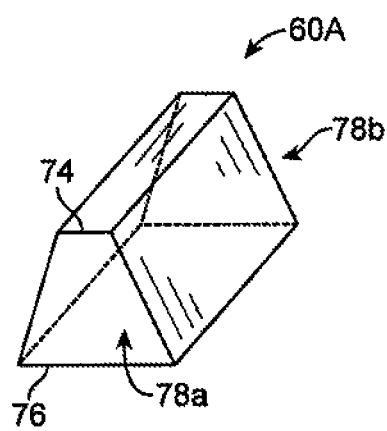
Figure 10D:
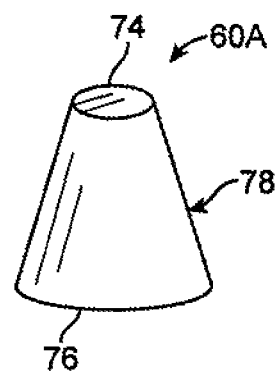
Figure 10E:
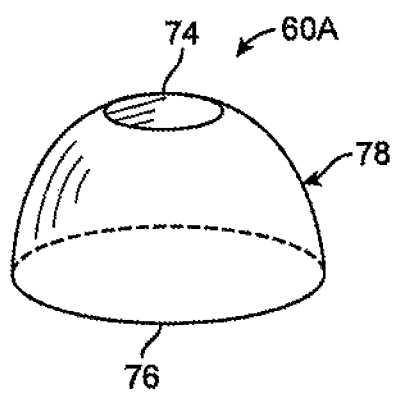

The inner surfaces 62A of a tapered through-hole 50A and the corresponding bioabsorbable depot 60A can take a number of shapes. FIGS. 10A-10E show various bioabsorbable depots 60A and it is to be understood that the inner surfaces of the tapered through-hole 50A has a corresponding negative shape to that shown in FIGS. 10A-10E. The tapered bioabsorbable depot 60A in FIGS. 9B-9D can have any of the three-dimensional shapes shown in FIGS. 10A-10D. The narrow end 74 of the bioabsorbable depot 60A corresponds in shape and dimension to the smaller opening 64A of the tapered through-hole 50A. The broader end 76 of the bioabsorbable depot 60A corresponds in shape and dimension to the larger opening 66A of the tapered through-hole 50A. The side surfaces 78 of the bioabsorbable depot 60A corresponds in shape and dimension to the inner surface 62A of the tapered through-hole 50A. Suitable tapered shapes include without limitation: a four-sided pyramidal shape as shown in FIG. 10A wherein none of the side surfaces 78 are parallel to another side surface; a three-sided pyramidal shape as shown in FIG. 10B; a trapezoidal shape as shown in FIG. 10C wherein two oppositely disposed side surfaces 78a, 78b are parallel to each other; a truncated cone shape as shown in FIG. 10D; and a truncated sphere shape as shown in FIG. 10E.

Figure 11A:
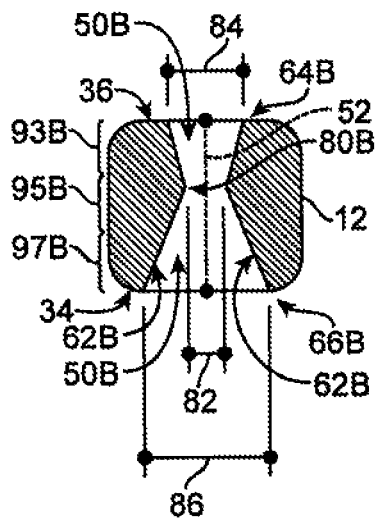
FIGS. 11A and 11B are cross-sectional and perspective views, respectively, of a prosthesis structural member, showing a through-hole with a depot retention feature in the form of a constriction in a middle segment of the through-hole.
Figure 11B:
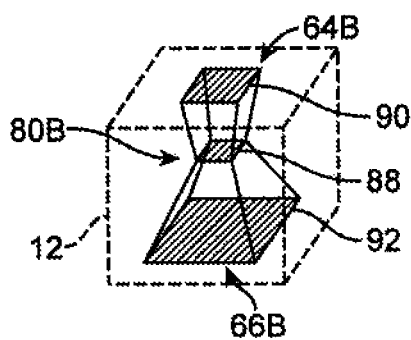

In some embodiments, as shown in FIGS. 11A and 11B, a constricted through-hole 50B (shown in FIG. 11A without a bioabsorbable depot) has an inner surface 62B with a depot retention feature in the form of a geometric constriction 80B between the opposite end openings 64B, 66B of the constricted through-hole 50B. As shown in FIG. 11A, the constriction 80B has a linear cross-dimension 82 that is smaller than the linear cross-dimensions 84, 86 of the end openings 64B, 66B. As shown in FIG. 11B, the constriction 80B has a planar cross-area 88 that is smaller than the planar cross-areas 90, 92 of the end openings 64B, 66B. For clarity in FIG. 11B, a prosthesis structural member 12, such as a stent strut, is illustrated as translucent with broken lines and the cross-areas are illustrated with hatch lines. As used herein, the "linear cross-dimension" and the "planar cross-area" are by definition perpendicular or substantially perpendicular to the end-to-end inline length 52 (illustrated as a broken line in FIG. 11A) of the through-hole. As indicated by the inline length 52 shown in FIG. 11A, the through-hole 50B extends end-to-end along a straight line.

Referring to FIG. 11A, the through-hole 50B includes end segments 93B, 97B at the opposite end openings 64B, 66B and a middle segment 95B between the end segments 93B, 97B. The geometric constriction 80B is located at the middle segment 95B and protrudes into the through-hole passageway. Indentations of the through-hole inner surface 62B are located above and below the geometric constriction 80B, at the opposite end openings 64B, 66B.

In some embodiments, the cross-dimension 82 of the constriction is from about 10 microns to 200 microns, more narrowly from about 10 microns to 100 microns, and more narrowly from about 5 microns to about 50 microns. The upper size limit for the constriction cross-dimension is preferably below 100 microns since debris of 100 microns or more in size may present a particular embolic hazard, which may then allow the opening cross-dimensions to be substantially greater than 100 microns. In some embodiments, the cross-dimension 82 of the constriction is at least half that of the cross-dimensions 84, 86 of the end opening, which gives an constriction-to-opening size ratio of 1-to-2. Other suitable ratios include without limitation 1-to-5, 1-to-4, 1-to-3, 2-to-3, 3-to-4, and 4-to-5.

In use, any one of the end openings 64B, 66B of the constricted through-hole 50B can be up against or immediately adjacent an anatomical structure, such as blood vessel wall. In FIG. 11A, the larger opening 66B of the through-hole 66B is located on the abluminal side of the prosthesis to allow delivery of a greater amount of a drug to a vessel wall. In other embodiments, the larger opening 66B of all or some of the through-holes 66B of a tubular intraluminal prosthesis can be located on the luminal side to allow delivery of a greater amount of a drug into a fluid stream passing through the central passageway of the prosthesis. In this way, the concentration of drug that is released from the prosthesis can be controlled and customized as desired.

Figure 12A:
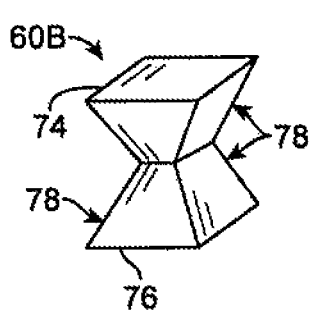
FIGS. 12A-12E are perspective views of various bioabsorbable depots that can be retained in a through-hole having a constriction in a middle segment of the through-hole.
Figure 12B:
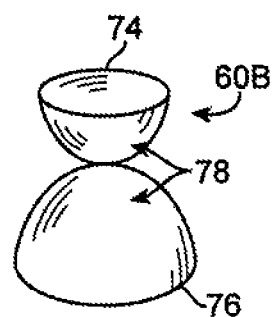
Figure 12C:
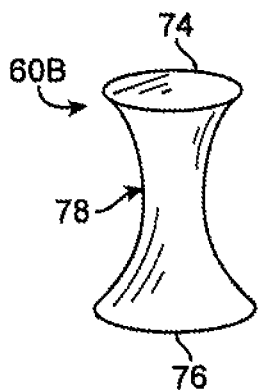
Figure 12D:
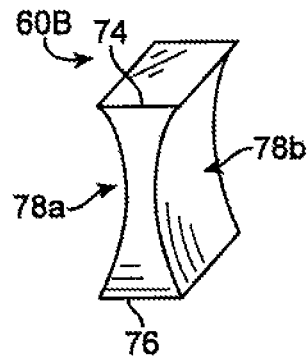
Figure 12E:
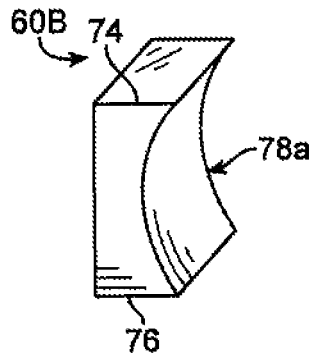

The inner surfaces 62B of a constricted through-hole 50B and the corresponding bioabsorbable depot 60B can take a number of shapes. FIGS. 12A-12E show various bioabsorbable depots 60B and it is to be understood that the inner surfaces of a constricted through-hole has a corresponding negative shape to that shown in FIGS. 12A-12E. The broad ends 74, 76 of the bioabsorbable depot 60B correspond in shape and dimension to the end openings of the constricted through-hole. The side surface 78 of the bioabsorbable depot 60B corresponds in shape and dimension to the inner surface of the constricted through-hole. For example, a smooth concave shape on the depot corresponds to a smooth convex shape on the inner surface of the through-hole, and vice versa. Suitable shapes include without limitation: a double pyramid as shown in FIG. 12A; a double truncated sphere as shown in FIG. 12B wherein two smooth concave surfaces meet at the constriction; a cylindrical concave shape as shown in FIG. 12C wherein a single concave sweep curve rotated 360 degrees defines the entire side surface 78; a double-concave bar as shown in FIG. 12D wherein only two side surfaces 78a, 78b are smooth and concave and the other side surfaces are planar; and a single-concave bar as shown in FIG. 12E wherein only one side surface 78a is smooth and concave and the other side surfaces are planar. The bioabsorbable depot 60B of FIG. 12A fits within the constricted through-hole 50B of FIGS. 11A and 11B.

In some embodiments, as shown in FIGS. 13A and 13B, a dilated or distended through-hole 50C (shown in FIG. 13A without a bioabsorbable depot) has an inner surface 62C with a depot retention feature in the form of a geometric distension 80C between the opposite end openings 64C, 66C of the distended through-hole 50C. As shown in FIG. 13A, the distension 80C has a linear cross-dimension 86 that is greater than the linear cross-dimensions 82, 84 of the end openings 64C, 66C. As shown in FIG. 13B, the distension 80C has a planar cross-area 88 that is larger than the planar cross-areas 90, 92 of the end openings 64C, 66C. For clarity in FIG. 13B, a prosthesis structural member 12, such as a stent strut, is illustrated as translucent with broken lines and the cross-areas are illustrated with hatch lines. As used herein, the "linear cross-dimension" and the "planar cross-area" are by definition perpendicular or substantially perpendicular to the end-to-end inline length 52 (illustrated as a broken line in FIG. 13A) of the through-hole. As indicated by the inline length 52 shown in FIG. 13A, the through-hole 50C extends end-to-end along a straight line. In use, any one of the narrow end openings 64C, 66C of the constricted through-hole 50C can be up against or immediately adjacent an anatomical structure, such as blood vessel wall.

Referring to FIG. 13A, the through-hole 50C includes end segments 93C, 97C at the opposite end openings 64C, 66C and a middle segment 95C between the end segments 93C, 97C. The geometric distension 80C, which can be described as an indentation of the through-hole inner surface 62C, is located at the middle segment 95C. The inner surface 62C protrudes inward toward the through-hole passageway, above and below the geometric distension 80C, at the opposite end openings 64C, 66C.

In some embodiments, both of the cross-dimensions 82, 84 of the end openings 64C, 66C are from about 10 microns to 200 microns, more narrowly from about 10 microns to 100 microns, and more narrowly from about 5 microns to about 50 microns. The upper size limit for the openings is optionally below 100 microns since debris of 100 microns or more in size may present a particular embolic hazard, which may then allow the distension cross-dimensions 86 to be substantially greater than 100 microns. In some embodiments, the distension cross-dimensions 86 is about 50 microns, or about 120 microns, or about 150 microns, or about 200 microns. In some embodiments, the opening cross-dimensions 82, 84 are at least half that of the distension cross-dimension 86, giving a size ratio of 1:2. Other suitable ratios include without limitation 1:4, 1:8 and 1:10.

The inner surfaces 62C of a distended through-hole 50C and the corresponding bioabsorbable depot 60C can take a number of shapes. FIGS. 14A-14E show various bioabsorbable depots 60C and it is to be understood that the inner surface of a distended through-hole has a corresponding negative shape to that shown in FIGS. 14A-14E. The narrow ends 74, 76 of the bioabsorbable depot 60C correspond in shape and dimension to end openings of the distended through-hole. The side surface 78 of the bioabsorbable depot 60C corresponds in shape and dimension to the inner surface of the distended through-hole. For example, a protrusion on the depot corresponds to an indentation on the inner surface of the through-hole, and vice versa. Suitable shapes include without limitation: a double pyramid as shown in FIG. 14A; a truncated sphere as shown in FIG. 14B; a cylindrical convex shape as shown in FIG. 14C wherein a convex sweep curve rotated 360 degrees defines the entire side surface 78; a double-convex bar as shown in FIG. 14D wherein only two side surfaces 78a, 78b are convex and the other side surfaces are planar; and single-convex bar as shown in FIG. 14E wherein only one side surface 78a is convex and the other side surfaces are planar. The bioabsorbable depot 60C of FIG. 14A fits within the distended through-hole 50C of FIGS. 13A and 13B.

Figure 15A:
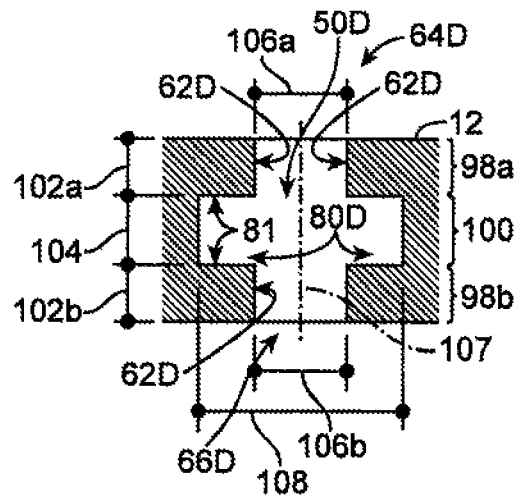
FIGS. 15A and 15B are cross-sectional views of a prosthesis structural member and a bioabsorbable depot, respectively, the views showing a groove formed in an inner surface of the through-hole for receiving and engaging a tang protruding from the bioabsorbable depot.

A depot retention feature of a through-hole 50 can be an indentation, groove, or depression in an inner surface of the through-hole. An indentation, groove, and depression with an abrupt change in geometry can be referred to as a notch retention feature 80D, which forms a notched inner surface 62, such as shown in FIG. 15A. Unlike randomly distributed pits and asperities of a rough surface, such as typically occurs with sintered materials, the depot retention features of the present invention are distributed in an ordered pattern in the inner surface of a through-hole or located in preselected areas on the inner surface. The location of pits and asperities of a sintered material and other rough surfaces are not selected, which could make such pits and asperities less reliable for depot retention. Also, the retention features of the present invention have a preselected shape, configuration, and dimension, which can make them more reliable for depot retention than pits and asperities having random sizes and shapes. For example, all the through-holes of an implantable prosthesis can each have a geometric retention feature that is identical or substantially identical for all the through-holes with respect to size, shape, dimension and/or location on the through-hole inner surface.

In some embodiments, as shown in FIG. 15A, a through-hole 50D has a notched inner surface 62D with a rectangular groove 80D formed therein. A bioabsorbable depot 60D is illustrated separately in FIG. 15B for clarity. It is to be understood that the bioabsorbable depot 60D (not illustrated in FIG. 15A) is disposed within the through-hole 50D. The bioabsorbable depot 60D can be in direct contact with the entire inner surface 62D of the through-hole 50D with no gaps. The inner surface 62D of the through-hole 50C has a corresponding negative shape to that shown for the bioabsorbable depot 60D. The bioabsorbable depot 60D has a tongue or tang 96 that protrudes out from the remainder of the depot. The tang 96 fits within and contacts the interior of the groove 80D to prevent the depot from sliding out of the through-hole.

Figure 15B:
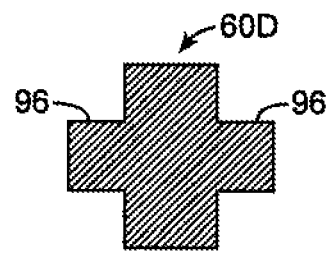
Figure 16A:
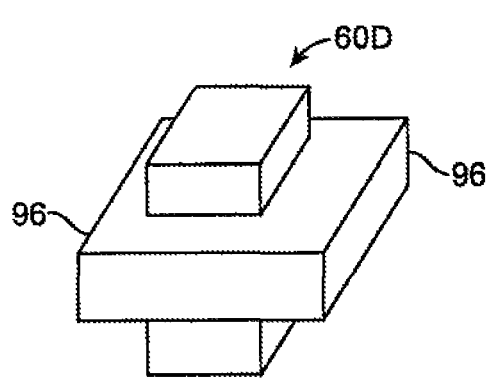
FIGS. 16A-16D are perspective views of various bioabsorbable depots that can be retained in the through-hole of FIG. 15A.
Figure 16B:
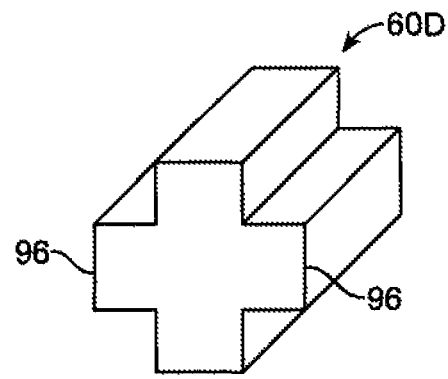
Figure 16C:
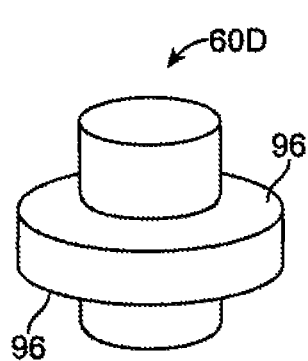
Figure 16D:
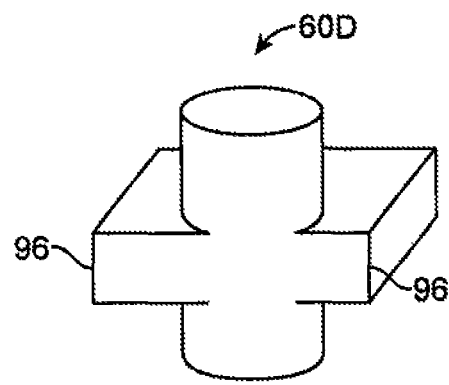

The cross-sectional shape for the bioabsorbable depot 60D of FIG. 15B can apply to any number of three-dimensional depot shapes, such as shown in FIGS. 16A-16D. Where the through-hole 50D is rectangular or four-sided, the groove 80D can sweep or extend through all four sides of the through-hole, as indicated by the shape of the corresponding tang 96 of the bioabsorbable depot 60D of FIG. 16A. Alternatively, the groove 80D can sweep or extend linearly through only two sides of a four-sided through-hole, as indicated by the shape of the corresponding tang 96 of the bioabsorbable depot 60D of FIG. 16B. It is also contemplated that the groove 80D can extend through only one side of the through-hole.

Where the through-hole 50D is circular or round, the groove 80D can sweep 360 degrees, entirely around a central passageway of the through-hole, as indicated by the shape of the corresponding circular tang 96 of the bioabsorbable depot 60D of FIG. 16C. Alternatively, the groove 80D can be a rectangular slot formed into a curved inner surface 62D of a circular through-hole 50D, as indicated by the bar-shaped tang 96 of the bioabsorbable depot 60D of FIG. 16D.

Referring again to FIG. 15A, the through-hole 50D comprises constricted regions or volumes 98a, 98b at both ends of the through-hole. A relatively broad or distended region or volume 100 is disposed between the constricted volumes 98. The constricted volumes 98a, 98b each have a preselected length or inline-dimension 102a, 102b, and a preselected width or cross-dimensions 106a, 106b. The distended volume 100 has a preselected length or inline-dimension 104 and a preselected width or cross-dimension 108. As used herein, each "inline-dimension" is measured along a straight line that is parallel to the central axis 107 of the through-hole, the central axis being a straight line running through the respective centers of the end openings 64d, 66d of the through-hole. Each "cross-dimension" is measured along a straight line that is perpendicular to the central axis 107. As indicated by the axis 107 shown in FIG. 15A, the through-hole 50D is symmetrical from side-to-side and extends end-to-end along a straight line.

Figure 15C:
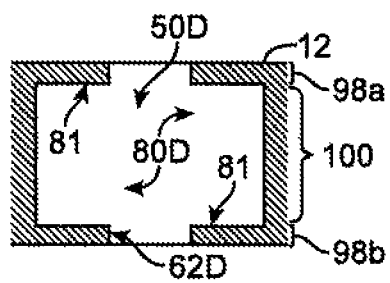
FIGS. 15C-15F are cross-sectional views of a prosthesis structural member, showing various groove geometries for retaining a bioabsorbable depot.

As shown in FIG. 15A, the inline-dimension 104 of the distended volume 100 and the inline-dimensions 98a, 98b of the constricted volumes 98a, 98b are substantially equal to each other. As shown in FIG. 15C, to facilitate greater retention capability and/or to carry more therapeutic agent in the bioabsorbable depot, the through-hole 50D can be configured such that the inline-dimension 104 of the distended volume 100 is substantially greater than the inline-dimensions 98a, 98b of the constricted volumes 98a, 98b. In this way, the distended volume 100 can be two, three, four or more times larger in volume than the combined volume of the constricted volumes 98a, 98b.

In some embodiments, both of the cross-dimensions 106a, 106b of the constricted volumes 98a, 98b are from about 10 microns to 200 microns, more narrowly from about 10 microns to 100 microns, more narrowly from about 10 microns to about 80 microns, and more narrowly from about 10 microns to about 50 microns. The upper size limit for the constricted cross-dimension is optionally below 100 microns since debris of 100 microns or more in size may present a particular embolic hazard, which may then allow the cross-dimensions 108 of the distended volume to be substantially greater than 100 microns.

Referring again to FIG. 15A, the cross-dimension 108 of the distended volume 100 is about twice that of the cross-dimensions 106a, 106b of the constricted volumes 98a, 98b. As shown in FIG. 15C, to facilitate greater depot retention capability and/or to carry more therapeutic agent in the bioabsorbable depot, the through-hole 50D can be configured such that the cross-dimension 108 of the distended volume 100 is about three times greater than the cross-dimensions 106a, 106b of the constricted volumes 98a, 98b, so as to provide a constricted-to-distended volumetric ratio of 1-to-3. Other suitable volumetric ratios include 3-to-4, 2-to-3; 1-to-2, and 1-to-4.

As shown in FIG. 15A, the cross-dimensions 106a, 106b of the constricted volumes 98a, 98b are substantially equal to each other. In other embodiments, the cross-dimension of one of the constricted volumes is substantially less than the cross-dimension of the constricted volume at the other end of the through-hole. This can facilitate greater retention capability when the smaller cross-dimension is on the luminal surface of an implanted tubular prosthesis and the larger cross-dimension is on the abluminal side against an anatomical lumen wall.

Figure 15D:
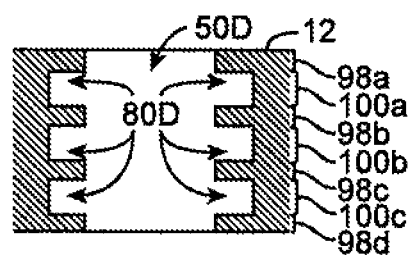

FIGS. 15A and 15C show embodiments having only one distended volume 100 in a through-hole 50D. In other embodiments, a through-hole can have any number of distended volumes separated from each other by constricted volumes so as to facilitate greater depot retention capability. As shown in FIG. 15D, for example, a through-hole 50D can have three distended volumes 100a, 100b, 100c and four constricted volumes 98a, 98b, 98c, 98b. This produces three sets of grooves 80D that are arranged in a repeating, non-random pattern in the inner surface of the through-hole 50D.

Figure 15E:
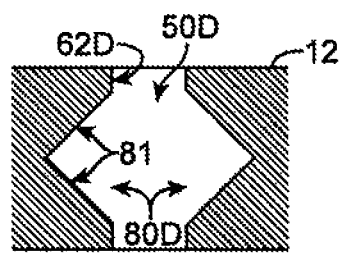

In other embodiments, the rectangular cross-sectional shape of the groove 80D as disclosed in FIGS. 15A, 15C and 15D can be replaced by any one or a combination of other cross-sectional shapes, including but not limited to a half-circle cross-sectional shape, a trapezoid cross-sectional shape, and a triangular cross-sectional shape such as that of the groove 80D in FIG. 15E.

In FIG. 15E, the point of the triangle extends into the inner surface of the through-hole. The interior surfaces 81 of the groove 80D are at oblique angles to other parts of the inner surface 62D. The term "oblique angle" refers to a direction that is not perpendicular and not parallel to a referenced structure. By comparison, in FIG. 15A various interior surfaces 81 of the rectangular groove 80D are at right angles or ninety-degree to other parts of the inner surface 62D.

Embodiments of the present invention include implantable prostheses having the through-holes described above wherein none, some, or all the through-holes are filled with a drug and/or drug-polymer composition. In some embodiments, the bioabsorbable depot may comprise multiple layers of bioabsorbable polymer, and any one or both of drug composition and polymer composition varies among the multiple layers. In other embodiments, the bioabsorbable depot comprises multiple layers of bioabsorbable polymer, and the bioabsorbable depot comprises drugs which may be in the same or different layers of the bioabsorbable polymer.

In some embodiments, a distended volume of the through-hole is filled or occupied in part or entirely by a first layer of a bioabsorbable depot, and a constricted volume of the through-hole is occupied in part or entirely by a second layer the bioabsorbable depot. The second layer optionally includes a bioabsorbable polymer that is either more resistant or less resistant to hydrolytic degradation of its mechanical properties or loss of strength, mass and/or molecular weight than a bioabsorbable polymer in the first layer. Either one or both of the first and second layers can contain a drug.

In some embodiments, a groove is filled or occupied in part or entirely by a first layer of a bioabsorbable depot. The layer may optionally include a bioabsorbable polymer that is either more resistant or less resistant to hydrolytic degradation of its mechanical properties or loss of strength, mass and/or molecular weight than a bioabsorbable polymer in a second layer of the bioabsorbable depot. Either one or both of the first and second layers can contain a drug. The second layer may be disposed entirely outside of the groove occupied by the first layer. In some embodiments, a tang or a protrusion of a bioabsorbable depot includes a bioabsorbable polymer that is more resistant to the above describe degradation than a bioabsorbable polymer in another part of the bioabsorbable depot. In this way, retention of the bioabsorbable depot in the through-hole may be enhanced. In FIG. 15D, for example, each of the distended volumes 100a, 100b, 100c can be filled by distinct layers of the bioabsorbable depot, each layer including a bioabsorbable polymer that is either more resistant or less resistant to the above described degradation than a bioabsorbable polymer in other distinct layers that fill the constricted volumes 98a, 98b, 98c.

The drug and/or drug-polymer composition can be deposited inside through-holes in a number of ways to form a stratified or multilayered depot or, alternatively, a unitary depot. For example, an implantable prosthesis with through-holes can be immersed in, painted with, or sprayed with a liquid containing a desired drug. The liquid can be a solution of the drug and a biodegradable polymer dissolved in a solvent. The liquid is allowed to pass into the through-holes and allowed to dry at room temperature or at an elevated temperature above room temperature. A composition of the drug and polymer remains after the solvent evaporates. The drug-polymer composition bonds or adheres to the walls of the through-holes. Excess amounts of the composition can be cleaned off all or some of the abluminal and/or luminal surfaces. Excess amounts of the composition can also be cleaned off all of the exterior surfaces (luminal, abluminal and side surfaces) of the implantable prosthesis so that the drug carried is carried exclusively in the through-holes.

Alternatively or in combination with the methods described above and below, drug and/or drug-polymer composition can be deposited into the through-holes by a method in which discrete droplets of liquid are discharged such that each droplet travels in a controlled trajectory. A system and method for depositing droplets having a controlled trajectory onto a stent is described in U.S. Pat. No. 7,208,190 to Verlee et al, which is incorporated herein by reference. In some embodiments, the controlled trajectory intersects selected abluminal, luminal, and side surfaces. In other embodiments, a feedback camera or optical device is implemented to insure that the drug is deposited only on the side surfaces and in the through-holes, so that abluminal and luminal surfaces are free of any drug. In other embodiments, the feedback camera or optical device is implemented to insure that the drug is deposited only in the through-holes, so that the drug is carried exclusively in the through-holes. A method of controlling where a drug is deposited by means of a feedback camera or optical device is described in U.S. Pat. No. 6,395,326 to Castro et al., which is incorporated herein by reference.

Alternatively or in combination with the methods described above, a pure drug and/or drug-polymer composition may be directly injected as a liquid into a through-hole by a hollow microneedle. The microneedle can be positioned immediately adjacent an end opening of the through-hole, then liquid of a predetermined volume from inside the microneedle can be forced into the through-hole. Alternatively or in combination with forced injection, the liquid from inside the microneedle can be drawn or imbibed into the through-hole by capillary action. For example, a droplet of liquid of a predetermined volume can be placed on an end opening of the through-hole, then capillary action brings the liquid inside through-hole.

The through-holes can be formed in the struts in a number of ways. In some embodiments, a laser is used to vaporize or otherwise remove material from the struts. The laser is aimed at a predetermined surface of a particular strut of a stent. To form a non-radial through-hole, such as a transverse or axial through-hole, the laser is aimed toward a side surface of a strut. To form a radial through-hole, the laser is aimed toward a luminal and/or abluminal surface of a strut. A laser system and method for making a stent is described in commonly owned U.S. Pat. No. 6,521,865 to Jones, et al., which is incorporated herein by reference.

After application of the laser, the resulting through-hole is bounded by the base material or substrate material of the stent strut. The phrase "substrate material" refers to the material at the core of the stent strut and does not include any coatings of other material added after initial formation of the core. The substrate material can be porous or, alternatively, substantially non-porous. The substrate material can be a fused particulate material or, alternatively, a non-particulate material. Non-particulate substrate materials can be made by extrusion, molding, and/or casting processes that mix molten material to form a substantially uniform and/or unitary core structure. By contrast, fused particulate materials are made up of discrete particles that are readily identifiable in the core structure after completion of the fusing step.

In some embodiments, each through-hole is bounded by or formed into a porous or particulate substrate material. A porous or particulate substrate material can be the result of particles of metal or polymer that have been sintered or fused together such that small gaps or pores remain between the fused particles. The through-holes of the present invention are different from conventional pores, pits, and/or asperities between sintered particles. Such pores are not located at predetermined positions on a stent strut as they are randomly distributed between particles. Also, such pores do not interconnect to form a channel or passageway in a selected direction. In many instances, such pores merely create surface roughness or sealed air pockets with no channel or pathway that extends straight through a structure.

Particles and pores of a sintered stent substrate can have an average diameter from submicron to tens of microns. In some embodiments, the through-holes formed into the stent substrate are several times larger in diameter than such pores. In some embodiments, the through-holes have an average diameter that is from 2 to 200 times larger than the average diameter of the pores of a sintered material, and more narrowly from 10 to 100 times larger than the average diameter of the pores of a sintered material, and more narrowly from 10 to 50 times larger than the average diameter of the pores of a sintered material.

Figure 17:
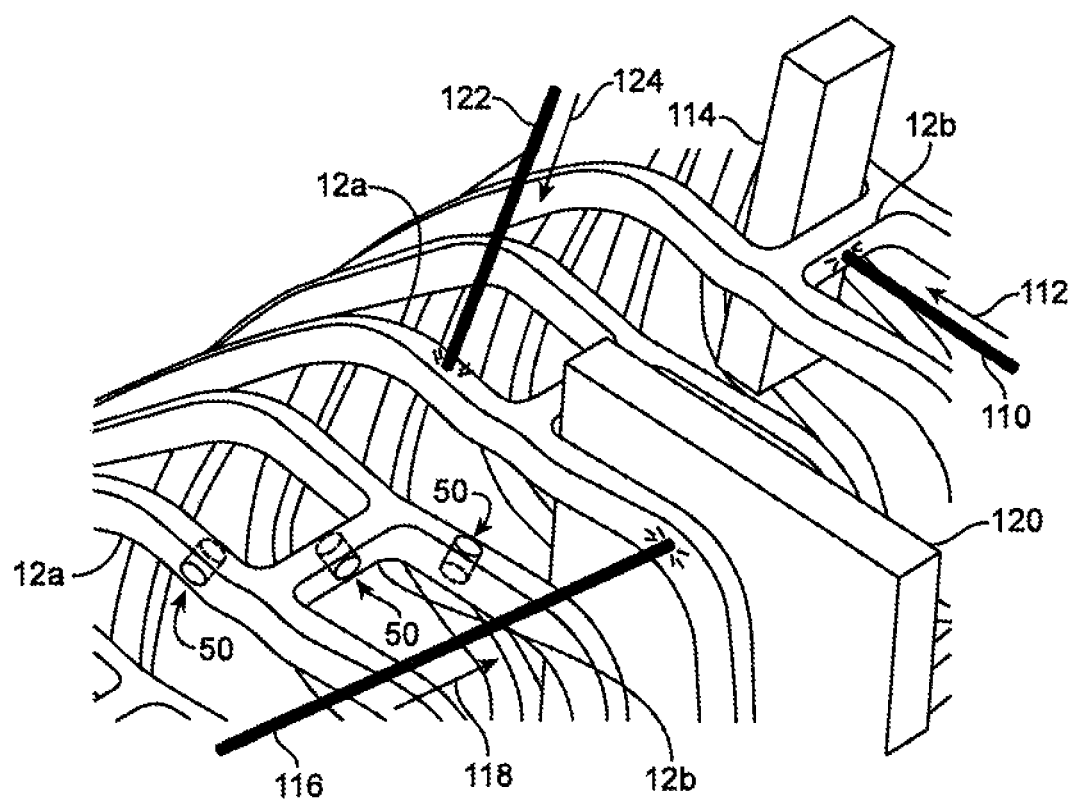
FIG. 17 is perspective view of a portion of a stent in an expanded state, showing laser beams making through-holes in the stent struts with shields protecting adjacent stent struts from the laser beams.

As shown in FIGS. 4 and 17, a laser beam 110 can be oriented in a transverse direction 112 relative to the central axis 18 of a stent to form a transverse through-hole. A shield 114, which can be in the form of a block of metal or ceramic, can be placed between the struts so that the laser beam forms a transverse through-hole in only a preselected strut and not in adjacent struts.

As shown in FIG. 17, a laser beam 116 can be oriented in a direction 118 that is at a slight angle, such as 5 degrees to 30 degrees, from the central axis of the stent to form an axial through-hole. Depending on the location of the strut, the laser beam can oriented at a direction that is substantially parallel to the stent central axis in order to form axial through-holes. A shield 120, which can be in the form of a metal or ceramic plate, can be placed between the struts so that the laser beam forms an axial through-hole in only a preselected strut and not in adjacent struts.

As shown in FIGS. 6 and 17, a laser beam 122 can be oriented in a radial direction 124 relative to the central axis 18 of a stent to form radial through-holes. A shield 126, which can be in the form of a metal rod, can be placed in the central passageway of the stent so that the laser beam forms a radial through-hole in only a preselected strut and not in other struts.

Various laser machining parameters can be tuned or adjusted in order to form the geometric retention feature of the through-hole. The angle of the laser beam to the surface being modified can be adjusted or selected to create the desired through-hole shape. The aspect ratio of the laser beam can be adjusted or selected to have a different width as a function of penetration into structure being modified. The direction, flow, and pressure of the gas being used to assist the laser cutting can also be adjusted. Any one or a combination of the above described parameters (e.g., laser angle, laser aspect ratio, gas direction, gas flow, gas pressure) can be adjusted or selected such that an inner surface of the through-hole is formed with any number of characteristics, including but not limited to tapered, concave, convex, notched, stepped, smooth, circular, and planar.

Figure 15F:
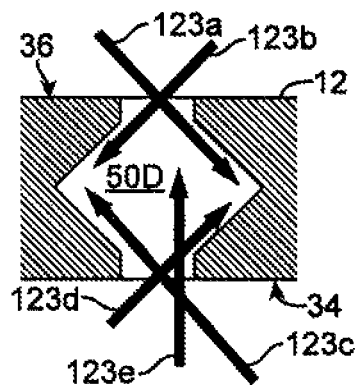

For example, as shown in FIG. 15F, a laser beam 123 can be applied in various directions at one region of a substrate material 12 to form a groove or distended volume in a through-hole 50d. A first laser beam 123a is used to form a first inner surface of the through-hole. A second laser beam 123b is used to form a second inner surface of the through-hole. A third laser beam 123c is used to form a third inner surface of the through-hole. A fourth laser beam 123d is used to form a fourth inner surface of the through-hole. Also, multiple laser beams can be applied simultaneously at one region of a substrate material 12 to form a groove or distended volume in a through-hole 50d. Also, a single laser beam can be directed into an abluminal surface 34 and rotated or tilted (from 123c to 123d) to form a plurality of inner surfaces, followed by or contemporaneously with another laser beam directed into a luminal surface 36 that is rotated or tilted (from 123a to 123b) to form another plurality of inner surfaces.

Alternatively, or in combination with any of the techniques described above and below, through-holes can be formed by electropolishing. For example, a through-hole formed by laser machining, as described above, can be subjected to electropolishing to make one of the end openings of the through-hole larger than the opposite end opening.

Alternatively, or in combination with any of the techniques described above and below, through-holes can be formed by electric discharge machining, also referred to as EDM. A method for creating features in an implantable prosthesis using EDM is described in commonly owned U.S. Pat. No. 7,537,610 to Reiss, which is incorporated herein by reference. An electrode and the prosthesis are electrically charged with opposite polarities. The prosthesis can be mounted over a mandrel or other support device and submerged in a dielectric fluid. The electrode is submerged in the dielectric fluid and brought into close proximity to the surface of the implantable prosthesis to be modified with a through-hole. A selected voltage level is applied across the electrode and the prosthesis that will result in electric discharges that vaporize or otherwise remove material from the surface of the prosthesis. An electrode having a selected tip shape can be used to form the desired shape of the through-hole. The electrode tip can have a shape that is a negative of the desired through-hole shape, so that as the electrode tip moves further and further below the prosthesis surface, inner surfaces of the through-hole attain the shape of the electrode tip.

The electrode tip can have any desired shape, including without limitation, the shapes shown in FIGS. 10A-10E. For example, in a first step, an electrode tip having the tapered, pyramid shape of FIG. 10A can be directed toward an luminal surface 36 of an implantable prosthesis to form a first end opening 64 of a through-hole. Next, in a second step, the same or another electrode tip can be directed toward an abluminal surface 34 at the same region of the prosthesis as in the first step. The second step forms a second end opening 66 directly opposite the first opening 64. In the second step, the electrode is moved deeper and deeper into the substrate material 12 until the hole being formed meets with the hole formed in the first step. The end result is the constricted through-hole 50B of FIG. 11A. It is contemplated that two or more electrodes can work simultaneously or sequentially on opposite surfaces (e.g., abluminal and luminal surfaces, or two opposite side surfaces) of a prosthesis structural member to form a through-hole with a geometric feature for depot retention. During the electrical discharge process, the one or more electrodes can be tilted and rotated inside a through-hole. Such tilting and rotation, can for example, correspond to numerals 123a-123e in FIG. 15F. Tilting and rotation enables the formation of other shapes, such as the tapered through-hole 50A and distended through-hole 50C of FIGS. 9A and 13A.

Alternatively, or in combination with any of the techniques described above and below, through-holes can be formed by etching a strut substrate material. The substrate material can be in the form of a sheet. Applied onto the sheet is a removable mask layer having a predetermined pattern of openings that corresponds to a desired pattern of non-radial through-holes. A chemical solution is applied so that unmasked areas of the sheet can be etched or eroded by the chemical to form one or more open channels or grooves in the sheet that corresponds to the desired pattern of non-radial through-holes. The sheet with grooves can be rolled up to form an inner layer of a tubular stent body. A second sheet of the substrate material can be used as an outer layer of the tubular stent body. After removal of the mask layer, the second sheet can be laminated, bonded or adhered over the rolled-up sheet so as to cover the grooves. A method for laminating layers of material to form a tubular prosthesis is described in U.S. Pat. No. 7,335,227 to Jalisi, which is incorporated herein by reference. A desired pattern of stent struts can be cut from the tube by a mechanical cutting tool or a laser. The resulting framework of interconnected struts will have the desired through-hole shape. Alternatively, a pattern of stent struts can be cut from the flat sheet of the substrate material after the etching step but before the sheet is rolled. Also, a pattern of stent struts can be cut from a flat sheet of the substrate before the etching step.

Figure 18A:
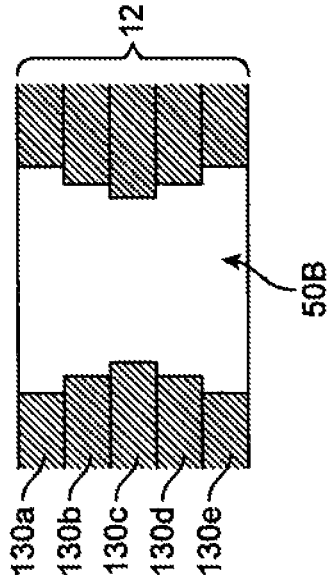
FIGS. 18A-18D are cross-sectional views of a prosthesis structural member, showing various stepped geometries for retaining a bioabsorbable depot, the geometries including tapered, convex, and notched inner surfaces of a through-hole.
Figure 18B:
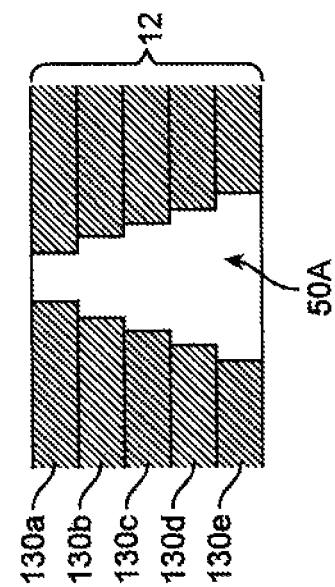
Figure 18C:
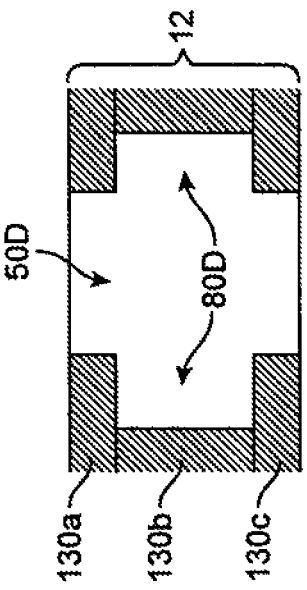
Figure 18D:
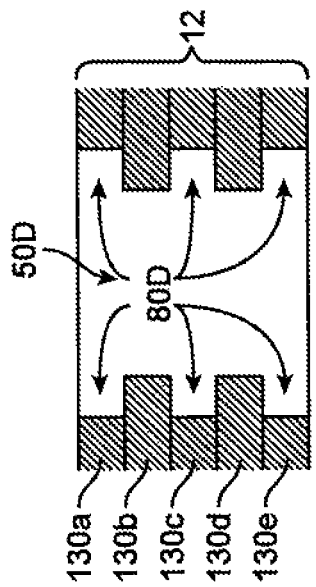

Any number of etched sheets 130 can be laminated or bonded as described above to form a number of geometries for a depot retention feature. The laminated or bonded etched sheets 30 collectively form a multi-layer substrate 12 of an implantable prosthesis, which is distinct from the unitary substrate of FIGS. 15A and 15C-15F. As shown in FIG. 18A, a plurality of sheets 130a-130e having progressively smaller holes can be stacked on top of each other to form a tapered through-hole 50A. As shown in FIG. 18B, a plurality of sheets 130a-130e having a variety of hole cross-dimensions can be stacked and aligned so as to form a convex or constricted through-hole 50B. As shown in FIGS. 18C and 18D, a plurality of sheets having a variety of hole cross-dimensions can be stacked so as to form notches or grooves 80D in an inner surface of a through-hole 50D. The sheets can have different thicknesses as shown in FIG. 18D.

In FIG. 18A-18D, the inner surfaces of the through-holes are non-continuous in that the surfaces include abrupt changes in geometry or geometric discontinuities. The geometric discontinuities are arranged in an ordered, predetermined pattern. In FIG. 18A, for example, the geometric discontinuities form an inner surface with progressive steps or ledges. The geometric discontinuities may be smoothed or eliminated by secondary processing, such as electropolishing, in order to form a smooth and continuous inner surface, such as the tapered inner surface of FIG. 9A or a smooth concave or convex surface.

Alternatively, or in combination with the techniques described above, a direct rapid prototyping method can be employed to form a stent having the above-described through-holes. Rapid prototyping refers to methods of automatically constructing three-dimensional objects from digital information derived from a computer-aided design file. The derived digital information can be in the form of an "STL" file, which is a file format used by stereolithography machines and the like. Rapid prototyping methods can make fully functional, production-quality objects in addition to prototypes. One rapid prototyping method involves depositing discrete or continuous amounts of a substrate material in multiple planar layers. The droplets adhere to each other so that each planar layer has a predetermined pattern of holes. The planar layers are formed successively on top of each other to build a three-dimensional tubular frame of interconnected struts with through-holes. The planar layers can, for example, correspond to numerals 130a-130e in FIGS. 18A-18D. It will thus be appreciated that any number of planar layers can be stacked and fused together to form various geometries for retaining a bioabsorbable depot. Rapid prototyping methods to form a stent according to the present invention also includes a Metal Printing Process (MPP), such as described in U.S. Patent Application Publication No. 2008/0057102 (U.S. application Ser. No. 11/839, 104), which is incorporated herein by reference.

Embodiments of the present invention include the above described configurations of through-holes, with or without a drug within the through-holes, in combination with a coating layer containing a drug. In some embodiments, the coating layer is on all external surfaces, including abluminal, luminal and side surfaces. In other embodiments, none of the coating layer is on any of the abluminal and luminal surfaces, and the coating layer is on one or more side surfaces exclusively. In other embodiments, none of the coating layer is on any of the abluminal surfaces, and the coating layer is on one or more side and luminal surfaces. In other embodiments, none of the coating layer is on any of the luminal surfaces, and the coating layer is on one or more of the side and abluminal surfaces.

It will be appreciated that through-holes can be provided in a number of implantable prostheses, including without limitation self-expandable stents, balloon-expandable stents, grafts, and stent-grafts. An implantable prosthesis is a device that is totally or partly introduced, surgically or medically, into a patient's body. The duration of implantation may be essentially permanent, i.e., intended to remain in place for the remaining lifespan of the patient; until the device biodegrades; or until the device is physically removed. An intraluminal prosthesis having through-holes can be configured for intraluminal delivery of a drug and can be configured to be implanted by intraluminal methods, such as by a catheter delivery device known in the art, or by other implantation methods.

An implantable medical device specifically designed and intended solely for the localized delivery of a therapeutic agent is within the scope of this invention. At present, a preferred implantable medical device comprises an intraluminal stent. Optionally, the stent has bare metal, uncoated struts having through-holes as described above, with a drug-polymer composition in the through-holes. The bare metal struts optionally have substantially smooth and non-porous external surfaces.

The substrate material of the prosthesis can be any suitable material known in the art of stents and other implantable devices. Substrate materials include without limitation nitinol or nickel-titanium alloys having shape memory and superelastic properties, other shape-memory metal alloys or polymers, stainless steel (such as 316L), nickel-cobalt-chromium-molybdenum alloys (such as MP35N), cobalt-chromium-tungsten-nickel-iron alloys (such as L605 or chonichrome), titanium, and tantalum.

The drug carried within and/or on the prosthesis substrate material can be any suitable therapeutic agent known in the art of stents and other implantable devices. The therapeutic agent can be in a substantially pure form. The therapeutic agent can be mixed, dispersed, dissolved, encapsulated or otherwise carried in a polymer.

Therapeutic agents include without limitation an anti-restenosis agent, an antiproliferative agent, an anti-inflammatory agent, an antineoplastic, an antimitotic, an antiplatelet, an anticoagulant, an antifibrin, an antithrombin, a cytostatic agent, an antibiotic, an anti-enzymatic agent, an angiogenic agent, a cyto-protective agent, a cardioprotective agent, a proliferative agent, an ABC A1 agonist, an antioxidant, a cholesterol-lowering agent, aspirin, an angiotensin-converting enzyme, a beta blocker, a calcium channel blocker, nitroglycerin, a long-acting nitrate, a glycoprotein IIb-IIIa inhibitor or any combination thereof.

Examples of antiproliferative agents include, without limitation, actinomycins, taxol, docetaxel, paclitaxel, rapamycin, 40-O-(3-hydroxy)propyl-rapamycin, 40-O-[2-(2-hydroxy)ethoxy]ethyl-rapamycin, or 40-O-tetrazole-rapamycin, 40-epi-(N1-tetrazolyl)-rapamycin, ABT-578, zotarolimus, everolimus, biolimus, novolimus, myolimus, deforolimus, temsirolimus, perfenidone and derivatives, analogs, prodrugs, co-drugs and combinations of any of the foregoing.

Examples of anti-inflammatory agents include, without limitation, both steroidal and non-steroidal (NSAID) anti-inflammatory agents such as, without limitation, clobetasol, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, ciclorofen, cintazone, cliprofen, clobetasol propionate, clobetasone butyrate, clopirac, cloticasone propionate, cormethasone acetate, cortodoxone, deflazacort, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, morniflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus, pimecrolimus and derivatives, analogs, prodrugs, co-drugs and combinations of any of the foregoing.

Examples of antineoplastics and antimitotics include, without limitation, paclitaxel, docetaxel, methotrexate, azathioprine, vincristine, vinblastine, fluorouracil, doxorubicin hydrochloride, and mitomycin.

Examples of antiplatelet, anticoagulant, antifibrin, and antithrombin drugs include, without limitation, sodium heparin, low molecular weight heparins, heparinoids, hirudin, argatroban, forskolin, vapiprost, prostacyclin, prostacyclin dextran, D-phe-pro-arg-chloromethylketone, dipyridamole, glycoprotein IIb/IIIa platelet membrane receptor antagonist antibody, recombinant hirudin and thrombin, thrombin inhibitors such as Angiomax ä, calcium channel blockers such as nifedipine, colchicine, fish oil (omega 3-fatty acid), histamine antagonists, lovastatin, monoclonal antibodies such as those specific for Platelet-Derived Growth Factor (PDGF) receptors, nitroprusside, phosphodiesterase inhibitors, prostaglandin inhibitors, suramin, serotonin blockers, steroids, thioprotease inhibitors, triazolopyrimidine, nitric oxide or nitric oxide donors, super oxide dismutases, super oxide dismutase mimetic, 4-amino-2,2,6,6-tetramethylpiperidine-1-oxyl (4-amino-TEMPO) and derivatives, analogs, prodrugs, codrugs and combinations thereof.

Examples of cytostatic agents include, without limitation, angiopeptin, angiotensin converting enzyme inhibitors such as captopril, cilazapril or lisinopril, calcium channel blockers such as nifedipine; colchicine, fibroblast growth factor (FGF) antagonists, fish oil (ω-3-fatty acid), histamine antagonists, lovastatin, monoclonal antibodies such as, without limitation, those specific for Platelet-Derived Growth Factor (PDGF) receptors, nitroprusside, phosphodiesterase inhibitors, prostaglandin inhibitors, suramin, serotonin blockers, steroids, thioprotease inhibitors, triazolopyrimidine (a PDGF antagonist) and nitric oxide.

While several particular forms of the invention have been illustrated and described, it will also be apparent that various modifications can be made without departing from the scope of the invention. It is also contemplated that various combinations or subcombinations of the specific features and aspects of the disclosed embodiments can be combined with or substituted for one another in order to form varying modes of the invention. Accordingly, it is not intended that the invention be limited, except as by the appended claims.

What is claimed is:

1. A method of making an implantable, intraluminal prosthesis, the method comprising:
   forming a tubular frame of interconnected structural members;
   forming through-holes in the structural members;
   forming an indentation in an inner surface of each of the through-holes; and
   forming a bioabsorbable depot in each of the through-holes, comprising forming a protrusion of the bioabsorbable depot that engages the indentation of the through-hole in which the bioabsorbable depot is retained, wherein engagement of the protrusion with the indentation prevents the bioabsorbable depot from sliding out an end opening of the through-hole, and wherein forming the protrusion is performed using a bioabsorbable polymer that is more resistant to hydrolytic degradation than a bioabsorbable polymer of another part of the bioabsorbable depot.

2. The method of claim 1, wherein the forming of the through-holes is performed after the forming of the tubular frame, and the forming of the indentation is performed after the forming of the through-holes.

3. The method of claim 1, wherein for each through-hole, the indentation is a concave surface.

4. The method of claim 1, wherein the forming of the through-holes comprises directing a laser toward the structural members to form an end opening of one of the through-holes, followed by changing the orientation angle of the laser relative to the structural members to form within the one of the through-holes a distended volume or a tapered inner surface.

5. The method of claim 1, wherein the tubular frame and the through-holes are formed by stacking layers of substrate material, each layer having a plurality of holes aligned with a plurality of holes of an immediately adjacent layer, the plurality of holes of at least one of the layers forming the indentations in the inner surfaces of the through-holes.

6. The method of claim 1, wherein forming the through-holes includes, for each through-hole, forming an end opening at a radially outward facing surface of the tubular frame and forming an end opening at a radially inward facing surface of the tubular frame.

7. The method of claim 1, wherein for each through-hole, the indentation is formed at a middle segment of the through-hole.

8. The method of claim 1, wherein for each through-hole, the indentation is a convex surface.

9. The method of claim 1, wherein for each through-hole, the indentation is a groove.

10. The method of claim 1, wherein the structural members form a plurality of ring structures configured to be crimped and subsequently radially expanded.

* * * * *